US011858869B2

(12) United States Patent
Finlayson et al.

(10) Patent No.: US 11,858,869 B2
(45) Date of Patent: Jan. 2, 2024

(54) METHODS OF INCREASING PLANT GROWTH AND/OR PRODUCTIVITY USING MICROBIAL INOCULANTS AND FERTILIZER COMPOSITIONS

(71) Applicant: Terragen Holdings Limited, Melbourne (AU)

(72) Inventors: Wayne Finlayson, Varsity Lakes (AU); Karen Jury, East Ballina (AU)

(73) Assignee: INTERNATIONAL MARKETING PARTNERSHIPS PTY LTD, Victoria (AU)

( * ) Notice: Subject to any disclaimer, the term of this patent is extended or adjusted under 35 U.S.C. 154(b) by 318 days.

(21) Appl. No.: 16/912,334

(22) Filed: Jun. 25, 2020

(65) Prior Publication Data

US 2021/0017096 A1  Jan. 21, 2021

Related U.S. Application Data

(63) Continuation of application No. 13/984,488, filed as application No. PCT/AU2012/001355 on Nov. 5, 2012, now abandoned.

(Continued)

(51) Int. Cl.
C05F 11/08 (2006.01)
C12N 1/20 (2006.01)
(Continued)

(52) U.S. Cl.
CPC .............. C05F 11/08 (2013.01); C05F 11/02 (2013.01); C05F 17/939 (2020.01); C12N 1/16 (2013.01);
(Continued)

(58) Field of Classification Search
CPC ........ C05F 11/08; C05F 11/02; C05F 17/939; C12N 1/16; C12N 1/165; C12N 1/20;
(Continued)

(56) References Cited

U.S. PATENT DOCUMENTS 4,604,125 A 8/1986 Robertiello et al.
4,985,060 A 1/1991 Higa
(Continued)

FOREIGN PATENT DOCUMENTS

CA 2792832 A1 * 9/2010 ............. A01N 63/02
CN 101717301 6/2010
(Continued)

OTHER PUBLICATIONS

Watanabe, *Lactobacillus kisonensis* sp. nov., *Lactobacillus otakiensis* sp. nov., *Lactobacillus rapi* sp. nov. and *Lactobacillus sunkii* sp. nov., Int'l J. of Systematic and Evolutionary Microbiology, 2009, vol. 59, pp. 754-760 (Year: 2009).*

(Continued)

Primary Examiner — Jennifer A Smith
(74) Attorney, Agent, or Firm — Casimir Jones, S.C.; Mary Ann D. Brow (57) ABSTRACT

Provided herein are methods for increasing plant growth, plant productivity and/or soil quality using microbial fertilizers comprising *Lactobacillus parafarraginis*, *Lactobacillus buchneri*, *Lactobacillus rapi*, *Lactobacillus zeae*, *Acetobacter fabarum* and *Candida ethanolica*.

17 Claims, 5 Drawing Sheets

Related U.S. Application Data (60) Provisional application No. 61/555,535, filed on Nov. 4, 2011.

(51) Int. Cl.

| | | |
|---|---|---|
| C12N 1/16 | (2006.01) | |
| C05F 11/02 | (2006.01) | |
| C05F 17/921 | (2020.01) | |
| C12R 1/02 | (2006.01) | |
| C12R 1/72 | (2006.01) | |
| C12R 1/225 | (2006.01) | |

(52) U.S. Cl.
CPC ............... *C12N 1/165* (2021.05); *C12N 1/20* (2013.01); *C12N 1/205* (2021.05); *C12R 2001/02* (2021.05); *C12R 2001/225* (2021.05); *C12R 2001/72* (2021.05); *Y02P 20/145* (2015.11); *Y02W 30/40* (2015.05)

(58) Field of Classification Search
CPC .......... C12N 1/205; C12N 11/02; C12N 1/00; C12R 2001/02; C12R 2001/225; C12R 2001/72; Y02P 20/145; Y02W 30/40; C09K 17/00; A01G 2/00
See application file for complete search history.

(56) References Cited

U.S. PATENT DOCUMENTS

| | | | |
|---|---|---|---|
| 5,605,557 | A | 2/1997 | Hall |
| 5,716,523 | A | 2/1998 | Powlen |
| 6,277,167 | B1 | 8/2001 | Ito et al. |
| 2003/0167811 | A1* | 9/2003 | Porubcan ............... C05F 3/00 71/6 |
| 2004/0192550 | A1 | 9/2004 | Sahasrabudhe |
| 2008/0213865 | A1* | 9/2008 | Lai ............... C12N 1/16 435/252.4 |
| 2009/0126432 | A1 | 5/2009 | Porubcan |
| 2011/0189147 | A1* | 8/2011 | Garner ............... A61K 35/74 424/93.45 |

FOREIGN PATENT DOCUMENTS

| | | | | |
|---|---|---|---|---|
| CN | 102173884 | A * | 9/2011 | ............... C05F 11/02 |
| EP | 2283810 | | 2/2011 | |
| KR | 100664747 | | 1/2007 | |
| RU | 2370956 | C1 * | 10/2009 | ............... C05D 9/02 |
| TW | 201035003 | A * | 10/2010 | ............... C05F 11/08 |
| WO | WO 2009038530 | | 3/2009 | |
| WO | WO 2011/012680 | | 2/2011 | |
| WO | WO-2011012680 | A2 * | 2/2011 | ............ A23G 1/002 |
| WO | WO-2011015425 | A1 * | 2/2011 | ............ A23G 1/0003 |

OTHER PUBLICATIONS

Ilse Cleenwerck, Acetobacter fabarum sp. nov., an acetic acid bacterium from a Ghanaian cocoa bean heap fermentation, Int'l J. of Systematic and Evolutionary Microbiology, 2008, vol. 68, pp. 2180-2185 (Year: 2008).*
Machine translation of CN-102173884-A (Year: 2011).*
Machine translation of TW201035003A (Year: 2010).*
Machine translation of RU-2370956-C1 (Year: 2009).*
Rojan P. John, R.D. Tyagi, S.K. Brar, R.Y. Surampalli & Danielle Prevost (2011) Bio-encapsulation of microbial cells for targeted agricultural delivery, Critical Reviews in Biotechnology, 31:3, 211-226, DOI: 10.3109/01388551.2010.513327 (Year: 2011).*
RHP, What are soil improvers?, (2016) (Year: 2016).*
By Vessey, J. Kevin, Plant growth promoting rhizobacteria as biofertilizers, Plant and Soil (2003) (Year: 2003).*
Chagas Junior, Gilson Celso Albuquerque, et al. "Identification of Lactic Acid Bacteria on Raw Material for Cocoa Bean Fermentation in the Brazilian Amazon." Fermentation 8.5 (2022): 199. (Year: 2022).*
Caicedo, Willan, and Derwin Viáfara. "Application of linear and nonlinear models for the temperature and pH behavior of a solid state fermented cocoa shell (*Theobroma cacao* L.)." (2019). (Year: 2019).*
Voidarou, Chrysa, et al. "Fermentative foods: Microbiology, biochemistry, potential human health benefits and public health issues." Foods 10.1 (2020): 69. (Year: 2020).*
Gutiérrez-Ríos, Hugo Gabriel, et al. "Yeasts as Producers of Flavor Precursors during Cocoa Bean Fermentation and Their Relevance as Starter Cultures: A Review." Fermentation 8.7 (2022): 331. (Year: 2022).*
Visintin, Simonetta, et al. "Molecular identification and physiological characterization of yeasts, lactic acid bacteria and acetic acid bacteria isolated from heap and box cocoa bean fermentations in West Africa." International Journal of Food Microbiology 216 (2016): 69-78. (Year: 2016).*
Rahim, Iradhatullah, et al. "Utilization of cocoa pod husk waste composting by *Tremella* sp and *Pleurotus* sp as a medium to growth of cocoa seedling." IOP Conference Series: Earth and Environmental Science. vol. 156. No. 1. IOP Publishing, 2018. (Year: 2018).*
Ashara et al., Protective effect of Lactobacillus casei strain Shirota against lethal infection with multi-drug resistant *Salmonella enterica* serovar Typhimurium DT104 in mice, J Appl Microbiol, 2011, 110: 163-173.
Chen et al., Isolation and identification of lactic acid bacteria from soil using an enrichment procedure. Applied Microbiology. 2005;40:195-200.
Claesson et al., The genus Lactobacillus—a genomic basis for understanding its diversity. FEMS Microbiol Lett. 2007;269:22-28.
Cleenwerck et al., *Acetobacter fabarum* sp. nov., an acetic acid bacterium from a Ghanaian cocoa bean heap fermentation. Int J Syst Evol Microbiol. Sep. 2008;58(Pt 9):2180-5.
Dijkshoorn et al., Strain, clone and species: comments on three basic concepts of bacteriology. J Med Microbiol. 2000;49:397-401.
Endo et al., *Lactobacillus farraginis* sp. nov. and *Lactobacillus parafarraginis* sp. nov., heterofermentative lactobacilli isolated from a compost of distilled shochu residue, International Journal of Systematic and Evolutionary Microbiology, 2007, 57:708-712.
Kuikui et al., Natural Lactic Acid Bacteria Population and Silage Fermentation of Whole-crop Wheat. Asian Australas. J Anim Sci. 2015;28:1123-1132.
Liu et al., Ch. 2 Biodiversity of Lactic Acid Bacteria. in Lactic Acid Bacteria. eds. Zhang and Cai. 2014 Springer Science + Business Media Dordrecht. 102 pages.
Nguyen et al., Soil-Borne Antagonists for Biological Control of Bacterial Wilt Disease Caused by Ralstonia solanacearum in Tomato and Pepper. Journal of Plant Pathology 2010; 92:395-406.
Tabacco et al. Dry matter and nutritional losses during aerobic deterioration of corn and sorghum silages as influenced by different lactic acid bacteria inocula, J Dairy Sci, 2011, 94: 1409-1419.
Watanabe et al., *Lactobacillus kisonensis* sp. nov., *Lactobacillus otakiensis* sp. nov., *Lactobacillus rapi* sp. nov., and *Lactobacillus sunkii* sp. nov., heterofermentative species isolated from sunki, a traditional Japanese pickle, Int J Syst Evol Microbiol, 2009, 59: 754-760.
Yanagida et al., Isolation and characterization of lactic acid bacteria from soils in vineyards. J Gen Appl Microbiol. 2005;51:313-318.
Yanagida et al., Isolation and characteristics of lactic acid bacteria from kashu vineyards in Japan. Lett Appl Microbiol. 2008;47:134-139.
Young et al., Encapsulation of plant growth-promoting bacteria in alginate beads enriched with humic acid, Biotechnol Bioeng, 2006, 95(1):76-83.
International Search Report and Written Opinion for PCT/AU2012/001355, dated Dec. 4, 2012.

* cited by examiner

METHODS OF INCREASING PLANT GROWTH AND/OR PRODUCTIVITY USING MICROBIAL INOCULANTS AND FERTILIZER COMPOSITIONS

This application is a continuation of U.S. patent application Ser. No. 13/984,488, filed Aug. 8, 2013, which is a § 371 National Entry of International Application No.: PCT/AU2012/001355, filed Nov. 5, 2012, which claims priority to U.S. Provisional Application No. 61/555,535 filed Nov. 4, 2011, each of which are herein incorporated by reference in their entireties.

FIELD OF THE ART

The present disclosure relates generally to microbial inoculants, particularly for use as fertilizers, comprising one or more microbial species or strains as described herein, and to fertilizer compositions comprising such organisms. The disclosure also relates to methods of promoting plant growth, increasing availability of nutrients in the soil and remediating degraded soils and pastures using microbial inoculants and fertilizer compositions of the present disclosure.

BACKGROUND

The use of fertilizers to enhance plant and crop production and overcome poor soil quality is widespread. Most commonly employed commercially available fertilizers are inorganic chemical fertilizers. Such chemical fertilizers can be expensive to produce, can be hazardous to use and are often associated with environmentally damaging consequences, such as nitrate contamination in run off and ground water. Environmental sustainability can be promoted by limiting the use of chemical fertilizers.

Fertilizer compositions comprising microorganisms (so-called "biofertilizers") are increasingly considered as alternatives to conventional chemical fertilizers. The ability of specific bacterial species to promote plant growth has long been recognised. For example, nitrogen-fixing bacteria such as *Rhizobium* species provide plants with essential nitrogenous compounds. Species of *Azotobacter* and *Azospirillum* have also been shown to promote plant growth and increase crop yield, promoting the accumulation of nutrients in plants. However bacteria of these genera are often unable to compete effectively with native soil and plant flora, thereby requiring the application of impractically large volumes of inoculum. Various *Bacillus* and *Pseudomonas* species have also found application in microbial-based fertilizers.

To date, biofertilizers have typically met with limited success, often not proving to be efficacious under real farming conditions. There remains a need for improved microbial-based fertilizers that are effective in providing nutrients for plant growth and are environmentally safe and nonhazardous.

SUMMARY OF THE DISCLOSURE

A first aspect of the present disclosure provides a microbial inoculant for use in increasing plant growth, plant productivity and/or soil quality, comprising strains of one or more bacterial species selected from *Lactobacillus parafarraginis*, *Lactobacillus buchneri*, *Lactobacillus rapi* and *Lactobacillus zeae*.

In a particular embodiments the inoculant comprises two of said *Lactobacillus* species, three of said *Lactobacillus* species or all of said *Lactobacillus* species. The inoculant may represent a symbiotic combination of two or more or three or more of said *Lactobacillus* species.

The *Lactobacillus parafarraginis* strain may be *Lactobacillus parafarraginis* Lp18. In a particular embodiment the *Lactobacillus parafarraginis* strain is *Lactobacillus parafarraginis* Lp18 deposited with National Measurement Institute, Australia on 27 Oct. 2011 under Accession Number V11/022945.

The *Lactobacillus buchneri* strain may be *Lactobacillus buchneri* Lb23. In a particular embodiment the *Lactobacillus buchneri* strain is *Lactobacillus buchneri* Lb23 deposited with National Measurement Institute, Australia on 27 Oct. 2011 under Accession Number V11/022946.

The *Lactobacillus rapi* strain may be *Lactobacillus rapi* Lr24. In a particular embodiment the *Lactobacillus rapi* strain is *Lactobacillus rapi* Lr24 deposited with National Measurement Institute, Australia on 27 Oct. 2011 under Accession Number V11/022947.

The *Lactobacillus zeae* strain may be *Lactobacillus zeae* Lz26. In a particular embodiment the *Lactobacillus zeae* strain is *Lactobacillus zeae* Lz26 deposited with National Measurement Institute, Australia on 27 Oct. 2011 under Accession Number V11/022948.

An inoculant of the first aspect may further comprise a strain of *Acetobacter fabarum*. The *Acetobacter fabarum* strain may be *Acetobacter fabarum* Af15. In a particular embodiment the *Acetobacter fabarum* strain is *Acetobacter fabarum* Af15 deposited with the National Measurement Institute, Australia on 27 Oct. 2011 under Accession Number V11/022943.

An inoculant of the first aspect may further comprise a yeast. The yeast may be a strain of *Candida ethanolica*. The *Candida ethanolica* strain may be *Candida ethanolica* Ce31. In a particular embodiment the *Candida ethanolica* strain is *Candida ethanolica* Ce31 deposited with the National Measurement Institute, Australia on 27 Oct. 2011 under Accession Number V11/022944.

One or more of the strains in the inoculant may be encapsulated. Where multiple strains are encapsulated, the strains may be individually encapsulated or combined in a single encapsulation.

A second aspect of the present disclosure provides a microbial inoculant comprising at least one *Lactobacillus* species, at least one *Acetobacter* species and at least one *Candida* species.

In a particular embodiment the at least one *Lactobacillus* species is selected from *Lactobacillus parafarraginis*, *Lactobacillus buchneri*, *Lactobacillus rapi* and *Lactobacillus zeae*. In a further particular embodiment, the microbial inoculant comprises at least one strain of each of said *Lactobacillus* species. In a further particular embodiment, the *Lactobacillus parafarraginis* is strain Lp18 (deposited under Accession Number V11/022945), *Lactobacillus buchneri* is strain Lb23 (deposited under Accession Number V11/022946), *Lactobacillus rapi* is strain Lr24 (deposited under Accession Number V11/022947) and *Lactobacillus zeae* is strain Lz26 (deposited under Accession Number V11/022948).

In a particular embodiment the at least one *Acetobacter* species is *Acetobacter fabarum*. In a further particular embodiment the *Acetobacter fabarum* is Af15 (deposited under Accession Number V11/022943).

In a particular embodiment the at least one *Candida* species is *Candida ethanolica*. In a further particular embodiment the *Candida ethanolica* is Ce31 (deposited under Accession Number V11/022944).

A third aspect of the present disclosure provides a microbial inoculant comprising at least one bacterial strain selected from *Lactobacillus parafarraginis* Lp18, *Lactobacillus buchneri* Lb23, *Lactobacillus rapi* Lr24 and *Lactobacillus zeae* Lz26.

An inoculant of the third aspect optionally further comprises *Acetobacter fabarum* Af15 and/or *Candida ethanolica* Ce31.

An inoculant of the first, second or third aspect may be used as a fertilizer.

A fourth aspect of the present disclosure provides a fertilizer composition comprising a microbial inoculant of the first, second or third aspect. The fertilizer composition may optionally comprise one or more additional components such as organic material, humic substances, penetrants, macronutrients, micronutrients and other soil and/or plant additives.

A fifth aspect of the present disclosure provides a method for increasing plant growth and/or productivity, the method comprising applying to the plant, plant seeds or to the soil in which the plant or plant seeds are grown an effective amount of a microbial inoculant of the first, second or third aspect or a fertilizer composition of the fourth aspect.

A sixth aspect of the present disclosure provides a method for improving soil quality, the method comprising applying to soil or to the plants or plant seeds in said soil an effective amount of a microbial inoculant of the first, second or third aspect or a fertilizer composition of the fourth aspect.

In accordance with the above aspects the plant may be, for example, a pasture plant, crop plant (including fruit and vegetable plants) or ornamental plant. The crop may be, for example, any human or animal food crop or crop for use as fuel or for pharmaceutical production. The food crop may be, for example, a fruit, vegetable, nut, seed or grain.

A seventh aspect of the present disclosure provides a method for remediating degraded soil or pasture, the method comprising applying to the soil or pasture an effective amount of a microbial inoculant of the first, second or third aspect or a fertilizer composition of the fourth aspect.

BRIEF DESCRIPTION OF THE DRAWINGS

Aspects and embodiments of the present disclosure are described herein, by way of non-limiting example only, with reference to the following drawings.

DETAILED DESCRIPTION

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, typical methods and materials are described.

The articles "a" and "an" are used herein to refer to one or to more than one (i.e., to at least one) of the grammatical object of the article. By way of example, "an element" means one element or more than one element.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The term "plant productivity" as used herein refers to any aspect of growth or development of a plant, that is a reason for which the plant is grown. Thus, for purposes of the present disclosure, improved or increased plant productivity refers broadly to improvements in biomass or yield of leaves, stems, grain, fruit, vegetables, flowers, or other plant parts harvested or used for various purposes, and improvements in growth of plant parts, including stems, leaves and roots. For example, when referring to food crops, such as grains, fruits or vegetables, plant productivity may refer to the yield of grain, fruit, vegetables or seeds harvested from a particular crop. For crops such as pasture, plant productivity may refer to growth rate, plant density or the extent of groundcover. "Plant growth" refers to the growth of any plant part, including stems, leaves and roots. Growth may refer to the rate of growth of any one of these plant parts.

The term "yield" refers to the amount of produced biological material and may be used interchangeably with "biomass". For crop plants, "yield" may also mean the amount of harvested material per unit of production or per area (e.g. hectare). Yield may be defined in terms of quantity or quality. The harvested material may vary from crop to crop, for example, it may be seeds, above-ground biomass, below-ground biomass (e.g. potatoes), roots, fruits, or any other part of the plant which is of economic value. "Yield" also encompasses yield stability of the plants. "Yield" also encompasses yield potential, which is the maximum obtainable yield under optimal growth conditions. Yield may be dependent on a number of yield components, which may be monitored by certain parameters. These parameters are well known to persons skilled in the art and vary from crop to crop. For example, breeders are well aware of the specific yield components and the corresponding parameters for the crop they are aiming to improve. For example, key yield parameters for potato include tuber weight, number of tubers, and number of stems per plant.

By "improving soil quality" is meant increasing the amount and/or availability of nutrients required by, or beneficial to plants, for growth. By way of example only, such nutrients include nitrogen, phosphorous, potassium, copper, zinc, boron and molybdenum. Also encompassed by the term "improving soil quality" is reducing or minimising the amount of an element that may be detrimental to plant growth or development such as, for example iron and manganese. Thus, improving soil quality by use of microbial inoculants and fertilizer compositions of the present disclosure thereby assists and promotes the growth of plants in the soil.

The term "remediating" as used herein in relation to degraded pasture or soil refers to the improvement in plant nutrient content in the soil to facilitate improved plant growth and/or yield. Degraded pasture includes overgrazed pasture.

As used herein, the term "effective amount" refers to an amount of microbial inoculant or fertilizer composition applied to a given area of soil or vegetation that is sufficient to effect one or more beneficial or desired outcomes, for example, in terms of plant growth rates, crop yields, or nutrient availability in the soil. An "effective amount" can be provided in one or more administrations. The exact amount required will vary depending on factors such as the identity and number of individual strains employed, the plant species being treated, the nature and condition of the soil to be treated, the exact nature of the microbial inoculant or fertilizer composition to be applied, the form in which the inoculant or fertilizer is applied and the means by which it is applied, and the stage of the plant growing season during which application takes place. Thus, it is not possible to specify an exact "effective amount". However, for any given case, an appropriate "effective amount" may be determined by one of ordinary skill in the art using only routine experimentation.

The term "crop" as used herein refers to any plant grown to be harvested or used for any economic purpose, including for example human foods, livestock fodder, fuel or pharmaceutical production (e.g. poppies).

The term "optionally" is used herein to mean that the subsequently described feature may or may not be present or that the subsequently described event or circumstance may or may not occur. Hence the specification will be understood to include and encompass embodiments in which the feature is present and embodiments in which the feature is not present, and embodiments in which the event or circumstance occurs as well as embodiments in which it does not.

In accordance with the present disclosure, novel microbial inoculants and microbial fertilizer compositions are presented which find application in increasing plant productivity and improving soil quality. In particular embodiments the microbial species present in the microbial inoculant or fertilizer composition provide a symbiotic combination of organisms.

In the broadest embodiments, a microbial inoculant of the present disclosure comprises strains of one or more bacterial *Lactobacillus* species. The *Lactobacillus* species may be selected from *Lactobacillus parafarraginis, Lactobacillus buchneri, Lactobacillus rapi* and *Lactobacillus zeae*. The inoculant may further comprise at least one *Acetobacter* species and at least one *Candida* species.

The *Lactobacillus parafarraginis* strain may be *Lactobacillus parafarraginis* Lp18. In a particular embodiment the *Lactobacillus parafarraginis* strain is *Lactobacillus parafarraginis* Lp18 deposited with National Measurement Institute, Australia on 27 Oct. 2011 under Accession Number V11/022945. The *Lactobacillus buchneri* strain may be *Lactobacillus buchneri* Lb23. In a particular embodiment the *Lactobacillus buchneri* strain is *Lactobacillus buchneri* Lb23 deposited with National Measurement Institute, Australia on 27 Oct. 2011 under Accession Number V11/022946. The *Lactobacillus rapi* strain may be *Lactobacillus rapi* Lr24. In a particular embodiment the *Lactobacillus rapi* strain is *Lactobacillus rapi* Lr24 deposited with National Measurement Institute, Australia on 27 Oct. 2011 under Accession Number V11/022947. The *Lactobacillus zeae* strain may be *Lactobacillus zeae* Lz26. In a particular embodiment the *Lactobacillus zeae* strain is *Lactobacillus zeae* Lz26 deposited with National Measurement Institute, Australia on 27 Oct. 2011 under Accession Number V11/022948.

The inoculant may further comprise a strain of *Acetobacter fabarum*. The *Acetobacter fabarum* strain may be *Acetobacter fabarum* Af15. In a particular embodiment the *Acetobacter fabarum* strain is *Acetobacter fabarum* Af15 deposited with the National Measurement Institute, Australia on 27 Oct. 2011 under Accession Number V11/022943.

The inoculant may further comprise a yeast. The yeast may be a strain of *Candida ethanolica*. The *Candida ethanolica* strain may be *Candida ethanolica* Ce31. In a particular embodiment the *Candida ethanolica* strain is *Candida ethanolica* Ce31 deposited with the National Measurement Institute, Australia on 27 Oct. 2011 under Accession Number V11/022944.

The concentrations of each microbial strain to be added to microbial inoculants and fertilizer compositions as disclosed herein will depend on a variety of factors including the identity and number of individual strains employed, the plant species being treated, the nature and condition of the soil to be treated, the exact nature of the microbial inoculant or fertilizer composition to be applied, the form in which the inoculant or fertilizer is applied and the means by which it is applied, and the stage of the plant growing season during which application takes place. For any given case, appropriate concentrations may be determined by one of ordinary skill in the art using only routine experimentation. By way of example only, the concentration of each strain present in the inoculant or fertilizer composition may be from about $1 \times 10^2$ cfu/ml to about $1 \times 10^{10}$ cfu/ml, and may be about $1 \times 10^3$ cfu/ml, about $2.5 \times 10^3$ cfu/ml, about $5 \times 10^3$ cfu/ml, $1 \times 10^4$ cfu/ml, about $2.5 \times 10^4$ cfu/ml, about $5 \times 10^4$ cfu/ml, $1 \times 10^5$ cfu/ml, about $2.5 \times 10^5$ cfu/ml, about $5 \times 10^5$ cfu/ml, $1 \times 10^6$ cfu/ml, about $2.5 \times 10^6$ cfu/ml, about $5 \times 10^6$ cfu/ml, $1 \times 10^7$ cfu/ml, about $2.5 \times 10^7$ cfu/ml, about $5 \times 10^7$ cfu/ml, $1 \times 10^8$ cfu/ml, about $2.5 \times 10^8$ cfu/ml, about $5 \times 10^8$ cfu/ml, $1 \times 10^9$ cfu/ml, about $2.5 \times 10^9$ cfu/ml, or about $5 \times 10^9$ cfu/ml. In particular exemplary embodiments the final concentration of the *Lactobacillus* strains is about $2.5 \times 10^5$ cfu/ml, the final concentration of *Acetobacter fabarum* may be about $1 \times 10^6$ cfu/ml and the final concentration of *Candida ethanolica* may be about $1 \times 10^5$ cfu/ml.

Also contemplated by the present disclosure are variants of the microbial strains described herein. As used herein, the term "variant" refers to both naturally occurring and specifically developed variants or mutants of the microbial strains disclosed and exemplified herein. Variants may or may not have the same identifying biological characteristics of the specific strains exemplified herein, provided they share similar advantageous properties in terms of promoting plant growth and providing nutrients for plant growth in the soil. Illustrative examples of suitable methods for preparing variants of the microbial strains exemplified herein include, but are not limited to, gene integration techniques such as those mediated by insertional elements or transposons or by homologous recombination, other recombinant DNA techniques for modifying, inserting, deleting, activating or silencing genes, intraspecific protoplast fusion, mutagenesis by irradiation with ultraviolet light or X-rays, or by treatment with a chemical mutagen such as nitrosoguanidine, methylmethane sulfonate, nitrogen mustard and the like, and bacteriophage-mediated transduction. Suitable and applicable methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bac-*

*terial Genetics*, Cold Spring Harbor Laboratory Press, Cold Spring Harbor, N.Y. (1992); and J. Sambrook, D. Russell, Molecular Cloning: A Laboratory Manual, 3rd ed., Cold Spring Harbor Laboratory Press, Cold Spring Harbor, N.Y. (2001), inter alia.

Also encompassed by the term "variant" as used herein are microbial strains phylogenetically closely related to strains disclosed herein and strains possessing substantial sequence identity with the strains disclosed herein at one or more phylogenetically informative markers such as rRNA genes, elongation and initiation factor genes, RNA polymerase subunit genes, DNA gyrase genes, heat shock protein genes and recA genes. For example, the 16S rRNA genes of a "variant" strain as contemplated herein may share about 85%, 86%, 87%, 88%, 89%, 90%, 91%, 92%, 93%, 94%, 95%, 96%, 97%, 98% or 99% sequence identity with a strain disclosed herein.

Microbial inoculants and fertilizer compositions of the present disclosure may optionally further comprise one or more additional microbial organisms, for example, additional agronomically beneficial microorganisms. Such agronomically beneficial microorganisms may act in synergy or concert with, or otherwise cooperate with the organisms of the present disclosure in the inoculant or fertilizer. Examples of agronomically beneficial microorganisms include *Bacillus* sp., *Pseudomonas* sp., *Rhizobium* sp., *Azospirillum* sp., *Azotobacter* sp., phototrophic and cellulose degrading bacteria, *Clostridium* sp., *Trichoderma* sp. and the like. Those skilled in the art will appreciate that this list is merely exemplary only, and is not limited by reference to the specific examples here provided.

In the soil environment, inoculated bacteria can find survival difficult among naturally occurring competitor and predator organisms. To aid in survival of microorganisms present in microbial inoculants and fertilizer compositions of the present disclosure upon application in the environment, one or more of the strains may be encapsulated in, for example, a suitable polymeric matrix. In one example, encapsulation may comprise alginate beads such as has been described by Young et al, 2006, Encapsulation of plant growth-promoting bacteria in alginate beads enriched with humic acid, *Biotechnology and Bioengineering* 95:76-83, the disclosure of which is incorporated herein by reference in its entirety. Those skilled in the art will appreciate that any suitable encapsulation material or matrix may be used. Encapsulation may be achieved using methods and techniques known to those skilled in the art. Encapsulated microorganisms can include nutrients or other components of the inoculant or fertilizer composition in addition to the microorganisms.

Those skilled in the art will appreciate that any plant may benefit from the application of microbial inoculants and fertilizer compositions of the present disclosure to soil, seeds and/or vegetation. Particular embodiments are employed to aid the growth, development, yield or productivity of crops and pastures or other plants of economic value, including ornamentals and plants grown for oils or biofuel. The crop plant may be, for example, a food crop (for humans or other animals) such as any fruit, vegetable, nut, seed or grain producing plant. Exemplary crop plants include, but are not limited to, tubers and other below-ground vegetables (such as potatoes, beetroots, radishes, carrots, onions, etc.), ground-growing or vine vegetables (such as pumpkin and other members of the squash family, beans, peas, asparagus, etc.), leaf vegetables (such as lettuces, chard, spinach, alfalfa, etc.), other vegetables (such as tomatoes, *brassica* including broccoli, avocadoes, etc.), fruits (such as berries, olives, stone fruits including nectarines and peaches, tropical fruits including mangoes and bananas, apples, pears, mandarins, oranges, mandarins, kiwi fruit, coconut, etc.), cereals (such as rice, maize, wheat, barley, millet, oats, rye etc.), nuts (such as macadamia nuts, peanuts, brazil nuts, hazel nuts, walnuts, almonds, etc.), and other economically valuable crops and plants (such as sugar cane, soybeans, sunflower, canola, sorghum, pastures, turf grass, etc).

Microbial inoculants and fertilizer compositions of the present disclosure may be applied directly to plants, plant parts (such as foliage) or seeds, or alternatively may be applied to soil in which the plants are growing or to be grown or in which seeds have been or are to be sown. Application may be by any suitable means and may be on any suitable scale. For example, application may comprise pouring, spreading or spraying, including broad scale or bulk spreading or spraying, soaking of seeds before planting, and/or drenching of seeds after planting or seedlings. Those skilled in the art will appreciate that multiple means of application may be used in combination (for example soaking of seeds prior to planting followed by drenching of planted seeds and/or application to seedlings or mature plants). Seeds, seedlings or mature plants may be treated as many times as appropriate. The number of applications required can readily be determined by those skilled in the art depending on, for example, the plant in question, the stage of development of the plant at which treatment is initiated, the state of health of the plant, the growth, environmental and/or climatic conditions in which the plant is grown and the purpose for which the plant is grown. For example, in the case of flowering crops such as tomatoes, it may be desirable to apply the microbial inoculant or fertilizer composition once or more than once during the flowering period.

Thus, in accordance with the present disclosure, microbial inoculants and fertilizer products as disclosed herein may be prepared in any suitable form depending on the means by which the inoculant or fertilizer composition is to be applied to the soil or to plant seeds or vegetation. Suitable forms can include, for example, slurries, liquids, and solid forms. Solid forms include powders, granules, larger particulate forms and pellets. Solid form fertilizer particles can be encapsulated in water soluble coatings (for example dyed or undyed gelatin spheres or capsules), extended release coatings, or by micro-encapsulation to a free flowing powder using one or more of, for example, gelatin, polyvinyl alcohol, ethylcellulose, cellulose acetate phthalate, or styrene maleic anhydride. Liquids may include aqueous solutions and aqueous suspensions, and emulsifiable concentrates.

In order to achieve effective dispersion, adhesion and/or conservation or stability within the environment of inoculants and fertilizer compositions disclosed herein, it may be advantageous to formulate the inoculants and compositions with suitable carrier components that aid dispersion, adhesion and conservation/stability. Suitable carriers will be known to those skilled in the art and include, for example, chitosan, vermiculite, compost, talc, milk powder, gels and the like.

Additional components may be incorporated into inoculants and fertilizer compositions of the present disclosure, such as humic substances, trace elements, organic material, penetrants, macronutrients, micronutrients and other soil and/or plant additives.

Humus or humic substances that may be incorporated may include, but are not limited to, humic acid derived from, for example oxidised lignite or leonardite, fulvic acid and humates such as potassium humate.

Organic material added may include, but is not limited to, biosolids, animal manure, compost or composted organic byproducts, activated sludge or processed animal or vegetable byproducts (including blood meal, feather meal, cottonseed meal, ocean kelp meal, seaweed extract, fish emulsions and fish meal).

Penetrants include, but are not limited to, non-ionic wetting agents, detergent based surfactants, silicones, and/or organo-silicones. Suitable penetrants will be known to those skilled in the art, non-limiting examples including polymeric polyoxyalkylenes, allinol, nonoxynol, octoxynol, oxycastrol, TRITON, TWEEN, Sylgard 309, Silwet L-77, and Herbex (silicone/surfactant blend).

Exemplary trace elements for inclusion in microbial inoculants and fertilizer compositions are provided in Example 1. However those skilled in the art will recognise that suitable trace elements are not limited thereto, and that any trace elements (natural or synthetic) may be employed.

Optional further soil and/or plant additives that can be added to inoculants and fertilizer compositions of the present disclosure include, for example, water trapping agents such as zeolites, enzymes, plant growth hormones such as gibberellins, and pest control agents such as acaracides, insecticides, fungicides and nematocides.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure will now be described with reference to the following specific examples, which should not be construed as in any way limiting the scope of the invention.

EXAMPLES

The following examples are illustrative of the invention and should not be construed as limiting in any way the general nature of the disclosure of the description throughout this specification.

Example 1—Microbial Strains

The following microbial strains were used in the production of a biofertilizer.

*Lactobacillus parafarraginis* Lp18 was isolated from an environmental source. Partial 16S rRNA sequencing indicated 100% similarity to *Lactobacillus parafarraginis* AB 262735 which has a risk group of 1 (TRBA). When cultured on MRS media for 3 days at 34° C., anaerobically, Lp18 produces cream, round, slight sheen, convex, colony diameter 1-2 mm (facultative anaerobe). Its microscopic appearance is Gram positive, non-motile, short rods rectangular, mainly diploid. *Lactobacillus parafarraginis* Lp18 was deposited with the National Measurement Institute, Australia on 27 Oct. 2011 under Accession Number V11/022945.

*Lactobacillus buchneri* Lb23 was isolated from an environmental source. Partial 16S rRNA sequencing indicated 99% similarity to *Lactobacillus buchneri* AB 429368 which has a risk group of 1 (TRBA). When cultured on MRS media for 4 days at 34° C., anaerobically, Lb23 produces cream, shiny, convex, colony diameter 1-2 mm (facultative anaerobe). Its microscopic appearance is Gram positive, non-motile, rods in chains. *Lactobacillus buchneri* Lb23 was deposited with the National Measurement Institute, Australia on 27 Oct. 2011 under Accession Number V11/022946.

*Lactobacillus rapi* Lr24 was isolated from an environmental source. Partial 16S rRNA sequencing indicated 99% similarity to *Lactobacillus rapi* AB 366389 which has a risk group of 1 (DSMZ). When cultured on MRS media for 4 days at 34° C., anaerobically, Lr24 produces cream, round, shiny colonies with a diameter of 0.5 mm (facultative anaerobe). Its microscopic appearance is Gram positive, non-motile, short rods single or diploid. *Lactobacillus rapi* Lr24 was deposited with the National Measurement Institute, Australia on 27 Oct. 2011 under Accession Number V11/022947.

*Lactobacillus zeae* Lz26 was isolated from an environmental source. Partial 16S rRNA sequencing indicated 99% similarity to *Lactobacillus zeae* AB 008213.1 which has a risk group of 1 (TRBA). When cultured on MRS media for 48 hours at 34° C., anaerobically, Lz26 produces white, round, shiny, convex, colonies with a diameter of 1 mm (facultative anaerobe). Its microscopic appearance is Gram positive, non-motile, short rods almost coccoid, diploid and some chains. *Lactobacillus zeae* Lz26 was deposited with the National Measurement Institute, Australia on 27 Oct. 2011 under Accession Number V11/022948.

*Acetobacter fabarum* Af15 was isolated from an environmental source. Partial 16S rRNA sequencing indicated 100% similarity to *Acetobacter fabarum* AM 905849 which has a risk group of 1 (DSMZ). When cultured on Malt extract media for 3 days at 34° C., AF15 produces opaque, round, shiny, convex, colony diameter 1 mm (aerobic). Its microscopic appearance is Gram negative, rods single or diploid. *Acetobacter fabarum* Af15 was deposited with the National Measurement Institute, Australia on 27 Oct. 2011 under Accession Number V11/022943.

*Candida ethanolica* Ce31 was isolated from an environmental source. Partial 16S rRNA sequencing indicated 89% similarity to *Candida ethanolica* AB534618. When cultured on Malt extract media for 2 days at 34° C., Ce31 produces cream, flat, dull, roundish, colony diameter 2-3 mm (aerobic). Its microscopic appearance is budding, ovoid yeast. *Candida ethanolica* Ce31 was deposited with the National Measurement Institute, Australia on 27 Oct. 2011 under Accession Number V11/022944.

Maintenance of Cultures

30% glycerol stocks were made of each isolate and maintained at −80° C. for long-term culture storage. Short-term storage of the cultures are maintained at 4° C. on agar slopes (3 month storage) and on agar plates which are subcultured monthly. To maintain the isolates original traits, a fresh plate is made from the −80° C. stock following three plate subcultures.

Inoculum and Growth Media

The *Lactobacillus* strains were grown with or without air (*L. rapi* prefers anaerobic) either in MRS broth (Difco) or on MRS agar plates depending on application. The cultures were routinely grown for 2 days at a mesophilic temperature of 30-34° C. The *Acetobacter* and *Ethanolica* strains are grown aerobically either in Malt extract broth (Oxoid) or on Malt extract agar plates depending on application. The cultures are routinely grown for 2 days at a mesophilic temperature of 30-34° C.

Fermenter 'Seed' Preparation

For individual strains, using a sterile nichrome wire a single colony is removed from a fresh culture plate and transferred to a universal bottle containing 15 mL of sterile media. The bottle is securely placed in a shaking incubator set at 30° C., 140 rpm for 48 hrs (*L. rapi* is not shaken). After incubation a cloudy bacterial growth should be visible. 'Seed' inoculation bottles are stored at 4° C. until required (maximum 1 week).

Typically a 5% bacterial inoculation is required for a fermenter run. The stored 15 ml culture seed is added to a Schott bottle containing a volume of sterile media which is 5% of the total fermenter working volume. The culture is incubated and shaken in the same way as the 15 ml seed. Large scale automatic fermenters are used to grow pure cultures of each isolate. There is an automatic feed of alkali, antifoam and glucose. Typically the temperature is maintained at 30-34° C., pH 5.5 but the oxygen and agitation varies depending on the microorganism.

Sample Analysis

After each large scale culturing of an isolate a sample is aseptically withdrawn and a viability count undertaken using 10 fold serial dilutions, performed in a laminar flow hood. A wet slide is also prepared and purity observed using a phase contrast microscope to double check for contaminants that may be present but unable to grow on the culture media. After 48 hours the viability plates are checked for a pure culture (same colony morphology) and the colonies counted to produce a colony forming unit per ml (cfu/ml) value. A Grams stain is also performed.

Example 2—Pasture Trials

Field trials on pasture were conducted using a biofertlizer as disclosed herein, in comparison to untreated pasture and pasture treated with conventional inorganic fertilizers.

The biofertilizer (hereinafter "IMP Bio") comprised the six microbial strains listed in Example 1, at final concentrations of $2.5 \times 10^5$ cfu/ml for each of the *Lactobacillus* strains, $1.0 \times 10^5$ cfu/ml for *Candida ethanolica* and $1.0 \times 10^6$ cfu/ml for *Acetobacter fabarum*. The strains were grown as described in Example 1 and mixed with 2% trace elements, 0.3% humate (Soluble Humate, LawrieCo), 3% molasses and 0.1-0.2% phosphoric acid. Phosphoric acid was added to the point where pH was in the range 3.8 to 4.0. The trace elements component typically comprised the following (per 1,000 L):

TABLE 1

Trace elements component of biofertilizer

| Material | Volume (kg) |
| --- | --- |
| Water | 200 kg |
| Potassium Sulphate | 15.25 kg |
| Copper Complex[1] | 25.6 kg |
| Magnesium Citrate[2] | 175.0 kg |
| Chromium Citrate[3] | 10.0 kg |
| Calcium Sokolate[4] | 52.0 kg |
| Citric Acid | 11.15 kg |
| Ferrous Sulphate | 4.0 kg |
| Cobalt Sulphate | 750 g |
| Nickel Sulphate | 250 g |
| Manganese Sulphate | 4.0 kg |
| Urea | 31.0 kg |
| Zinc Sulphate | 4.0 kg |
| Borax | 4.5 kg |
| M A P | 13.25 kg |
| Sodium Molybdate | 2.5 kg |
| Acetic Acid | 10.8 kg |
| Sugar | 50.0 kg |

Conventional inorganic fertilizers used as comparators were Spray Gro Liquid Urea, DAP (diammonium phosphate), and 14:16:11 commercial NPK mix.

Sites for the pasture trials were selected based on rainfall levels, soil type, pasture composition and past fertilizing practices. The following locations in Tasmania were used: Nabageena (high rainfall; rye grass, cocksfoot, Yorkshire fog and other grasses), Cuprona (high rainfall; rye grass), West Moorville/Upper Burnie (high rainfall; rye grass), Connorville (dryland pasture; degraded) and Connorville (irrigated pasture; rye grass).

At each location, multiple 4×10 m strips of pasture were prepared by mowing to a height of 45 mm (and removal of clipped plant material prior to fertilizing). At West Moorville/Upper Burnie and Nabageena, IMP Bio was applied to replicate plots at 20 L/ha, 30 L/ha or 50 L/ha, and 14:16:11 NPK mix was applied to replicate plots at 250 kg/ha. At West Moorville, DAP was also applied to replicate plots at 125 kg/ha. At Cuprona, IMP Bio was applied to replicate plots at 20 L/ha, 30 L/ha or 50 L/ha, and Spray Gro Liquid Urea was applied at 50 L/ha. At Connorville, IMP Bio was applied to replicate plots at 20 L/ha, 30 L/ha or 50 L/ha, and DAP was applied to replicate plots at 125 kg/ha. IMP Bio and SprayGro Urea were applied as large droplets through 2 m backpack boom sprays in a single pass. 14:16:11 NPK mix and DAP were applied by hand distribution. At each location, replicate control (unfertilized) plots were set aside.

Plant yield and leaf nutrient content were analysed 6-8 weeks after treatment.

Results for plant yield are shown in Table 2 below. These results indicate that the IMP Bio fertilizer produced yields at least similar to, and in some cases superior to, conventional inorganic fertilizers.

TABLE 2

Yield (kg/ha/day)

| Area | Control | Conventional fertilizer | IMP Bio (30 L/ha) | IMP Bio (half strength) |
| --- | --- | --- | --- | --- |
| Cuprona | 65 | 79 (Spray Gro) | 75 | — |
| Nabageena | 60 | 78 (14:16:11) | 73 | — |
| Connorville (dryland) | 35 | 34 (DAP) | 32 | 31 |
| Connorville (irrigated) | 44 | 56 (DAP) | 51 | 44 |
| West Moorville | 67 | 90 (DAP) | 87 | — |

Plant material nutrient analysis was conducted, as shown in Table 3 below. Key elements required by, or beneficial to, the pasture for growth (such as nitrogen, phosphorous, potassium, calcium, copper, zinc, boron, molybdenum) were present in plant material from the IMP Bio treated plots at levels equivalent to or higher than those plots treated with the comparator conventional inorganic fertilizer, despite these nutrients not being added in the IMP Bio fertilizer.

TABLE 3

| Nutrient | Control | Conventional fertilizer | IMP Bio (30 L/ha) |
| --- | --- | --- | --- |
| Connorville (irrigated) | | | |
| Nitrogen (%) | 1.95 | 2.23 | 1.94 |
| Phosphorus (%) | 0.28 | 0.38 | 0.26 |
| Potassium (%) | 2.61 | 2.69 | 2.53 |
| Sulphur (%) | 0.26 | 0.27 | 0.24 |
| Carbon (%) | 43.5 | 43.7 | 43.8 |
| Calcium (%) | 0.33 | 0.30 | 0.41 |
| Magnesium (%) | 0.28 | 0.25 | 0.28 |
| Sodium (%) | 0.24 | 0.45 | 0.30 |

TABLE 3-continued

| Nutrient | Control | Conventional fertilizer | IMP Bio (30 L/ha) |
|---|---|---|---|
| Copper (ppm) | 4.2 | 4.5 | 5.3 |
| Zinc (ppm) | 19 | 21 | 24 |
| Manganese (ppm) | 372 | 339 | 309 |
| Iron (ppm) | 113 | 90 | 109 |
| Boron (ppm) | 4.9 | 4.7 | 6.0 |
| Molybdenum (ppm) | 0.7 | 0.7 | 0.7 |
| Cobalt (ppm) | 0.2 | 0.1 | 0.2 |
| Silicon (ppm) | 201 | 169 | 193 |
| Nitrogen:Sulphur ratio | 7.4 | 8.4 | 8.1 |
| Nitrogen:Phopshorus ratio | 7.0 | 5.9 | 7.4 |
| Nitrogen:Potassium ratio | 0.7 | 0.8 | 0.8 |
| Carbon:Nitrogen ratio | 22.3 | 19.6 | 22.6 |
| Crude protein (% N × 6.25) | 12.2 | 13.9 | 12.1 |
| West Moorville | | | |
| Nitrogen (%) | 1.56 | 1.57 | 1.64 |
| Phosphorus (%) | 0.34 | 0.33 | 0.31 |
| Potassium (%) | 2.26 | 2.43 | 2.11 |
| Sulphur (%) | 0.25 | 0.24 | 0.24 |
| Carbon (%) | 44.0 | 44.1 | 43.9 |
| Calcium (%) | 0.78 | 0.59 | 0.57 |
| Magnesium (%) | 0.24 | 0.20 | 0.18 |
| Sodium (%) | 0.18 | 0.14 | 0.15 |
| Copper (ppm) | 4.8 | 4.3 | 4.7 |
| Zinc (ppm) | 18 | 18 | 19 |
| Manganese (ppm) | 37 | 33 | 35 |
| Iron (ppm) | 172 | 114 | 120 |
| Boron (ppm) | 10 | 7.7 | 8.3 |
| Molybdenum (ppm) | 1.3 | 1.0 | 1.1 |
| Cobalt (ppm) | 0.1 | <0.1 | <0.1 |
| Silicon (ppm) | 316 | 268 | 244 |
| Nitrogen:Sulphur ratio | 6.2 | 6.5 | 7.0 |
| Nitrogen:Phopshorus ratio | 4.5 | 4.7 | 5.3 |
| Nitrogen:Potassium ratio | 0.7 | 0.6 | 0.8 |
| Carbon:Nitrogen ratio | 28.2 | 28.1 | 26.8 |
| Crude protein (% N × 6.25) | 9.8 | 9.8 | 10.2 |
| Cuprona | | | |
| Nitrogen (%) | 3.68 | 3.60 | 3.68 |
| Phosphorus (%) | 0.39 | 0.38 | 0.39 |
| Potassium (%) | 3.43 | 3.43 | 2.90 |
| Sulphur (%) | 0.38 | 0.41 | 0.41 |
| Carbon (%) | 43.6 | 44.2 | 43.6 |
| Calcium (%) | 0.51 | 0.49 | 0.58 |
| Magnesium (%) | 0.24 | 0.27 | 0.26 |
| Sodium (%) | 0.26 | 0.36 | 0.44 |
| Copper (ppm) | 8.7 | 9.1 | 8.4 |
| Zinc (ppm) | 24 | 25 | 22 |
| Manganese (ppm) | 106 | 118 | 74 |
| Iron (ppm) | 104 | 110 | 103 |
| Boron (ppm) | 6.2 | 4.2 | 4.4 |
| Molybdenum (ppm) | 0.3 | 0.3 | 0.9 |
| Cobalt (ppm) | <0.1 | <0.1 | <0.1 |
| Silicon (ppm) | 267 | 284 | 214 |
| Nitrogen:Sulphur ratio | 9.8 | 8.8 | 9.1 |
| Nitrogen:Phopshorus ratio | 9.5 | 9.5 | 9.3 |
| Nitrogen:Potassium ratio | 1.1 | 1.1 | 1.3 |
| Carbon:Nitrogen ratio | 11.8 | 12.3 | 11.9 |
| Crude protein (% N × 6.25) | 23.0 | 22.5 | 23.0 |

Example 3—Soil Quality

To determine the effect of a biofertilizer as disclosed herein on soil quality, 2×150 g of soil from a farm in Tasmania were each weighed into 2× clean 150 ml Schott bottle. 10 mls of a 1:10 dilution of IMP Bio fertilizer (see Examples 1 and 2) was dripped over the top of the soil in one bottle and the lid replaced and incubated at 34° C. for one week. The second bottle had no biofertilizer added was incubated 34° C. The soil from both bottles was analysed by Environmental Analytical Laboratories (EAL, Southern Cross University Lismore, NSW) using standard soil testing methods.

The results for the one week treatment of soil with IMP Bio are summarised in Table 4. Soil tests on the untreated incubated sample are not shown as these were substantially the same as the initial untreated soil test. It is clear from the soil tests on the two treated samples that there is a marked difference in the soil after incubation with IMP Bio. The second sample analysed, shows a general trend of increasing the levels of available cations (calcium, magnesium, potassium, sodium and all trace elements—zinc, manganese, iron and copper) and ammonium nitrogen, while the total levels under the acid extractions were slightly lower across all nutrients. Organic matter increased by 1% (14.6% to 15.5%) between the samples dates. The overall decrease in total nutrients does not appear to be significant.

There was a greater than three-fold increase in ammonium nitrogen, although no increase in nitrates. This indicates an increase in mineralisation of nitrogen from the organic nitrogen pool, and may be linked to the transformation of organic material, the level of which in this soil is particularly high. This could also indicate nitrogen fixation.

TABLE 4

| Nutrient/soil characteristic | Prior to IMP Bio treatment | After IMP Bio treatment |
|---|---|---|
| Calcium (mg/kg) | 1006 | 1431 |
| Magnesium (mg/kg) | 181 | 279 |
| Potassium (mg/kg) | 218 | 317 |
| Phosphorus (mg/kg) | 2.2 | 3.3 |
| Nitrate nitrogen (mg/kg) | 13.3 | 14.2 |
| Ammonium nitrogen (mg/kg) | 21.2 | 72.6 |
| Sulfur (mg/kg) | 28.5 | 33.8 |
| Zinc (mg/kg) | 3.0 | 3.6 |
| Manganese (mg/kg) | 19 | 48 |
| Iron (mg/kg) | 335 | 369 |
| Copper (mg/kg) | 3.4 | 3.5 |
| Boron (mg/kg) | 0.82 | 0.98 |
| Silicon (mg/kg) | 24 | 28 |
| Total carbon (%) | 8.33 | 8.85 |
| Total nitrogen (%) | 0.52 | 0.53 |
| Carbon:Nitrogen ratio | 16.1 | 16.6 |
| Organic matter (%) | 14.6 | 15.5 |
| pH | 6.41 | 6.36 |
| Conductivity (dS/m) | 0.132 | 0.202 |

Example 4—Potato Trials

A field trial was conducted in which Bondi variety potatoes were treated with the IMP Bio biofertilizer (see Example 2) at planting. The trial was conducted at Waterhouse, Tasmania. IMP Bio was applied in furrows to rows 30 m long at a rate of 50 L/ha, either alone, or together with the conventional chemical fertilizer 5-10-16 at either 650 kg/ha (delivering 32 kg/ha nitrogen, 63 kg/ha phosphorus and 100 kg/ha potassium) or 1250 kg/ha (delivering 63 kg/ha nitrogen, 125 kg/ha phosphorus and 200 kg/ha potassium). In a fourth replicate, 5-10-16 was applied at 1250 kg/ha together with the fungicide Amistar. Four plots of 4 m length were dug from each treatment and tubers assessed for size and yield. The results are shown in Table 5.

TABLE 5

Potato yield

| Treatment | Total yield >45 g (t/ha) | Seed (t/ha) | Yield >350 g (t/ha) | Yield <45 g (t/ha) | Stems/plant |
|---|---|---|---|---|---|
| IMP Bio | 42.4 | 38.1 | 4.3 | 2.9 | 3.7 |
| IMP Bio + 5-10-16 (650 kg/ha) | 39.2 | 35.4 | 3.8 | 1.7 | 3.3 |
| IMP Bio + 5-10-16 (1250 kg/ha) | 35.6 | 30.0 | 5.6 | 1.6 | 3.3 |
| 5-10-16 + Amistar | 39.3 | 33.4 | 5.9 | 1.8 | 3.2 |

There was an increase in stem numbers per plant in the IMP Bio treatment, which is desirable (higher stem numbers typically correlating with higher tuber numbers). The reduction in large (>350 g) tubers observed with IMP Bio treatment is also significant as larger tubers have lower commercial value than seed sized tubers (45-350 g). Additionally, the 14% increase (5 tonnes/ha) in seed weight in the IMP Bio compared to the 5-10-16+Amistar treatment is also of significant economic value. The IMP Bio treated potato plants were also observed to be approximately three weeks more developed (in terms of maturity) than those treated with 5-10-16.

Example 5—Tick Bean Trials

A greenhouse experiment was conducted to establish the effect of IMP Bio biofertilizer (see Example 2) on tick bean plant growth, compared to the commercial fertilizer Baileys TriStar (8.3% N, 0% P, 16% K, 14% S, 1% Fe, 2% Mg).

The treatment groups and regimes employed for seedlings post-germination were as follows:
Control: 300 µl water
"T40": 300 µl TriStar at 40 L/ha
"SGL40": 300 µl IMP Bio at 40 L/ha
"T25% GL40": 300 µl TriStar 25% plus IMP Bio at 40 L/ha
"GL40": 300 µl IMP Bio at 40 L/ha Seeds in the T40, SGL40 and T25% GL40 groups were soaked for 1 hour in 100 ml of a 1:10 dilution of IMP Bio solution prior to planting. Control and GL40 seeds remained dry prior to planting. Three replicates of each treatment group (and two replicates of the control group) were used. Seeds were planted 5 mm deep in the middle of each pot and the pots placed in a temperature-controlled greenhouse at 16-18° C. under hydroponic lights. After germination, all seedlings were treated every two weeks (for a total of four weeks) using the treatments described above. Seedlings were watered once a day.

Figure 1:
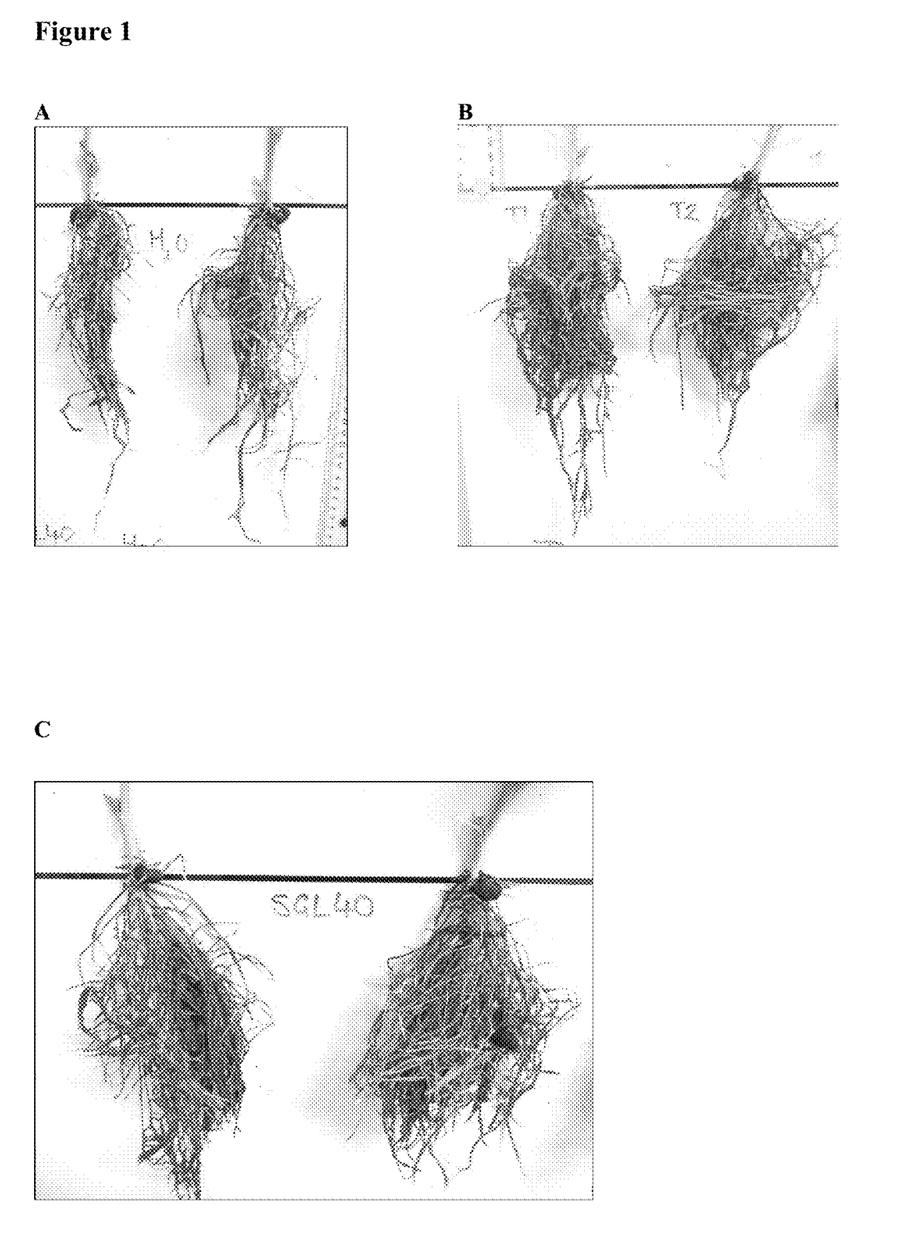
FIG. 1. Root development in tick bean plants, treated as described in Example 5. A, control group; B, T40 treatment group; C, SGL40 treatment group; D, T25% GL40 treatment group; E, GL40 treatment group.

At the conclusion of the experiment it was observed that the tallest plants, and the plants with the strongest main stem were those of the T25% GL40 treatment group. Overall, the best growth was observed in the T25% GL40 and SGL40 groups (data not shown). However the most noticeable differences observed were in root development (see FIG. 1). Roots of the control plants were the least dense and the shortest (FIG. 1A). Roots of the T40 plants had good root density and length (FIG. 1B), however development was not as extensive as in the plants treated with IMP Bio. In the SGL40 plants the root system shown good density and length (FIG. 1C). Root nodules were present as were black nodule-like growths. In the T25% GL40 plants the root system was more dense and longer than in other treatment groups (FIG. 1D). Root nodules were present but black nodule-like growth was not seen. In the GL40 plants the root system was similarly dense, long and well developed (FIG. 1E). Root nodules were present as were black nodule-like growths.

Example 6—Tomato Trials

A greenhouse experiment was conducted to investigate the effect of IMP Bio biofertilizer (see Example 2) on the growth rate of tomato plants over a 20 day period. Tomato seedlings were provided by Cedenco. Water only was used as a control, and the commercial fertilizer FlowPhos (Yara Nipro) used as a comparator. Seedlings were potted into 50 mm pots in one of three different soils obtained from different locations (Cedenco) and drenched once with either: (i) 10 ml water; (ii) 10 ml of IMP Bio (100 ml in 900 ml water); (iii) 10 ml of FlowPhos (7.5 ml in 900 ml water); or (iv) 10 ml of FlowPhos plus IMP Bio (7.5 ml FlowPhos and 100 ml IMP Bio made to a total volume of 1000 ml with water). Three replicates of the control (water) group and eight replicates of each of the treatment groups. Plants were watered twice a day with 30 ml water. Plant height was measured every third day over the 20 day period of the experiment.

Figure 2:
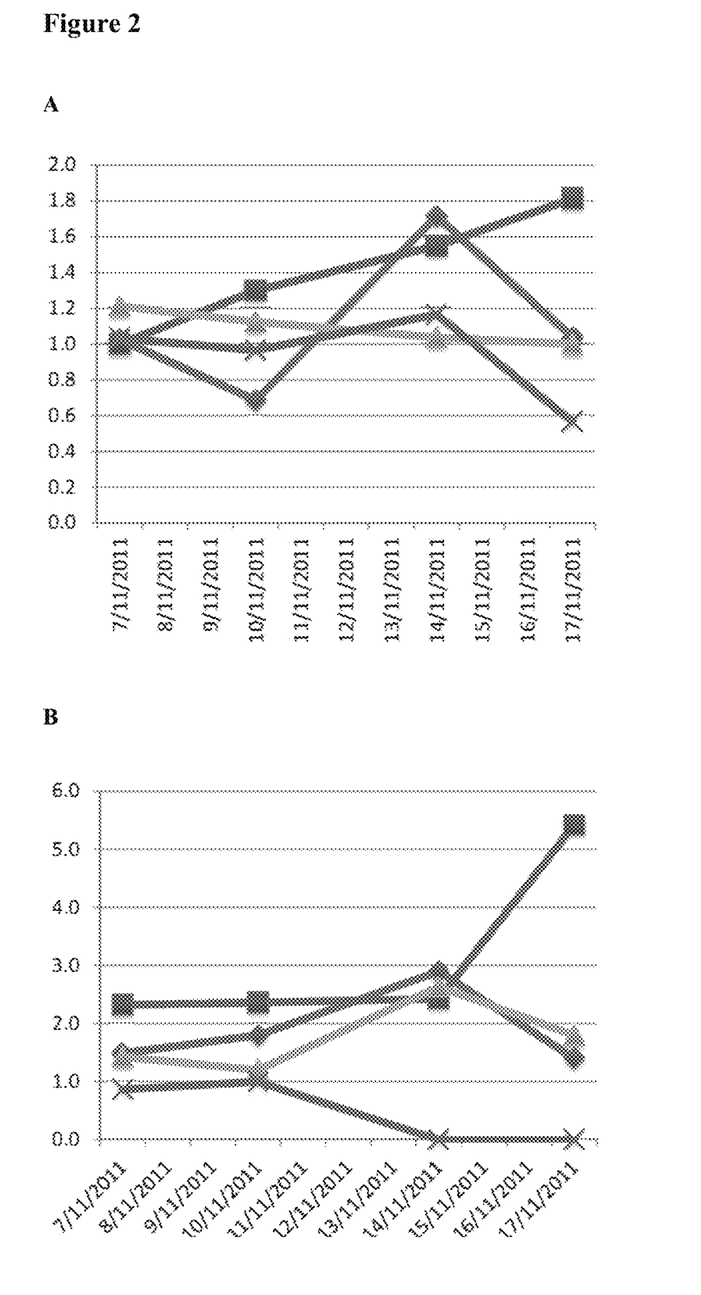
FIG. 2. Average rate of change of growth (height) of tomato plants over a 20 day treatment period in three different soils (A-C), treated as described in Example 6. Squares represent IMP Bio treated seedlings, diamonds represent FlowPhos treated seedlings, triangles represent IMP Bio plus FlowPhos treated seedlings, crosses ('x') represent untreated (water only) seedlings.
Figure 3:
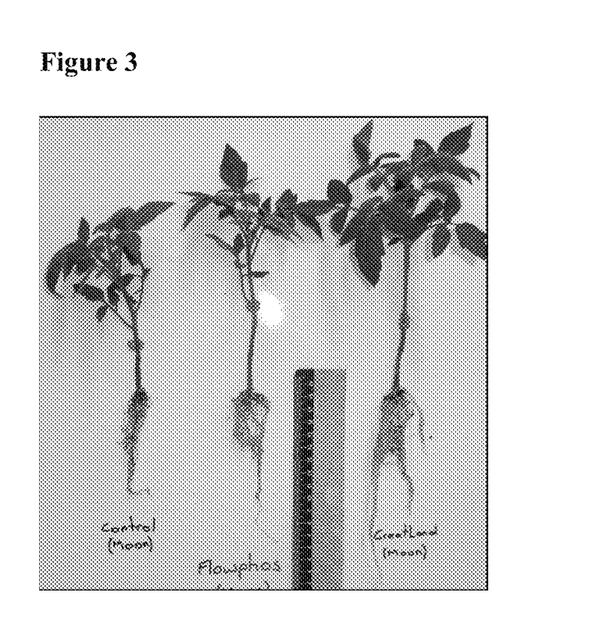
FIG. 3. Comparison of plant height, foliage size and root development in tomato seedlings, treated as described in Example 6. GreatLand=IMP Bio treated seedling.

The average rate of change of growth (height) of tomato seedlings over the 20 day period for all treatment groups, in each of the three soils, is shown in FIG. 2. As can be seen, the IMP Bio treated plants were the only plants that consistently showed increases in growth over the course of the experiment, resulting in taller plants. FIG. 3 shows an exemplary comparison of difference in plant height, foliage and root system development in control plants, FlowPhos treated plants and IMP Bio (GreatLand) treated plants, in which the advantages of IMP Bio treatment are clearly evident.

A field trial was then conducted at Timmering, Victoria in which tomato plants were treated with IMP Bio by foliar application during flowering, either at a rate of 80 L/ha or 40 L/ha during early flowering followed by 40 L/ha during mid flowering. Yield of tomato fruit was determined and compared to the yield from the same number of untreated plants. For the plants that received 80 L/ha IMP Bio, total fruit yield was 149.87 tonnes/ha, compared to 128.87 tonnes/ha for the untreated plants. For the plants that received two applications of 40 L/ha IMP Bio, total fruit yield was 130.15 tonnes/ha, compared to 103.05 tonnes/ha for the untreated plants.

Example 7—Macadamia Trials

A field trial was conducted in which macadamia trees in a 100 ha farm in Lismore, NSW were treated with the IMP Bio biofertilizer (see Example 2) by spraying at the rate of 40 L/ha, every 2-3 months for a period of 12 months. IMP Bio was applied in conjunction with chemical fertilizer (Easy N Fertilizer), the same fertilizer used for at least the previous four years. The yield of macadamia nuts following the 12 month treatment was approximately 70 tonnes, compared to an average yield of 35 tonnes per year over the previous four years. The benefits offered by the IMP Bio biofertilizer allowed for a significant reduction in the application of chemical fertilizer.

Leaf and soil analysis was also conducted at four sites across the farm after 45 days of IMP Bio use. Significant increases were observed in levels of zinc, manganese, iron and boron in macadamia leaves, and in ammonium nitrogen, nitrate nitrogen, phosphorus, potassium, calcium, copper and boron in the soil.

Example 8—Strawberry Trials

Figure 4:
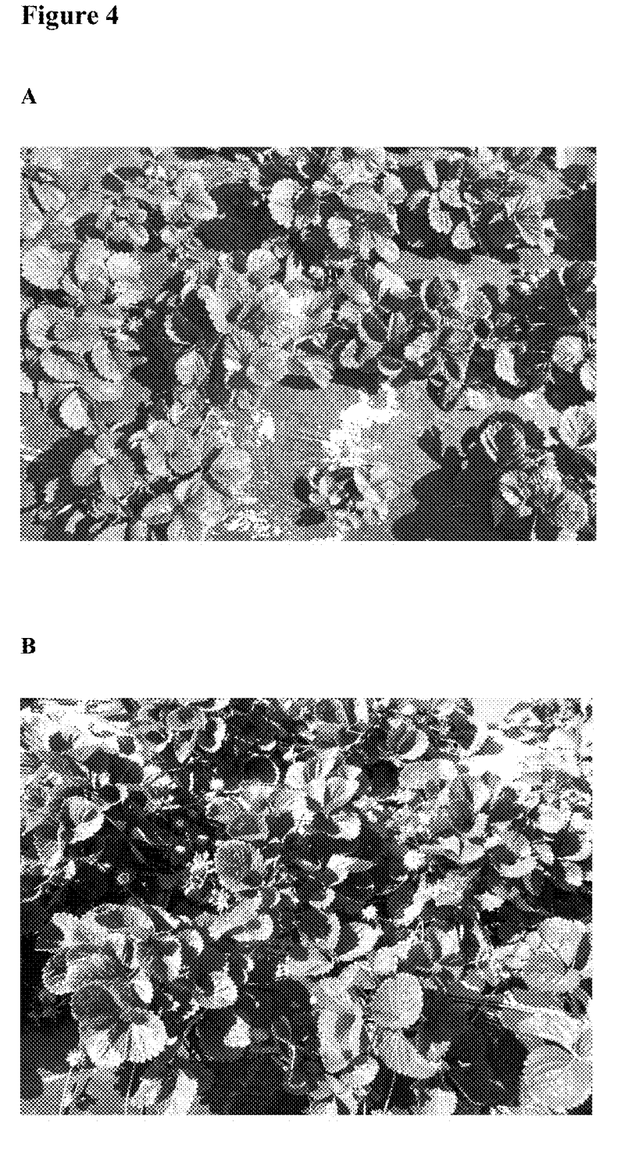
FIG. 4. Comparison of vegetative growth (and density of growth) of strawberry plants, treated as described in Example 8. A, conventional fertilizer treated plants after 3 months. B, IMP Bio treated plants after 3 months.

A field trial was conducted in Beerwah, Qld to establish the effect of IMP Bio biofertilizer (see Example 2) on strawberry plant growth and fruit yield over an 8 ha plot. The IMP Bio was applied at a rate of 40 L/ha to the soil pre-planting, again at the same rate at planting, and weekly during the vegetative growth and flowering stage (weeks 2-4), during the fruiting stage (weeks 5-8) and during the picking stage (weeks 9-16). In comparison to conventional fertilizer (NitroPhoska (blue) applied preplanting at 1000 kg/ha), plant growth rate was significantly increased and plants showed increased vegetative growth and leaf area (FIG. 4). Fruit yield was also significantly increased (38,000 kg as compared to 20,000 kg).

Example 9—Other Trials

Preliminary trials have also been conducted on sugar cane, lettuce, raspberries, roses, wheat, basil and turf grass (golf course green). In each case IMP Bio biofertilizer (see Example 2) was observed to result in increased rate of growth of plants compared to untreated plants (data not shown).

The invention claimed is:

1. A method, comprising:
   i) providing a microbial fertilizer composition comprising strains of *Lactobacillus parafarraginis, Lactobacillus buchneri, Lactobacillus rapi, Lactobacillus zeae, Acetobacter fabarum,* and *Candida ethanolica;*
   ii) treating plant seeds or seedlings with an amount of the microbial fertilizer composition; and
   iii) growing the treated plant seeds or seedlings in soil to produce plants,
   wherein the amount of the microbial fertilizer composition is effective to increase growth and/or productivity of the plants.

2. The method according to claim 1, wherein the strain of *Lactobacillus parafarraginis* is *Lactobacillus parafarraginis* Lp18 deposited with National Measurement Institute, Australia on 27 Oct. 2011 under Accession Number V11/022945; wherein the strain of *Lactobacillus buchneri* is *Lactobacillus buchneri* Lb23 deposited with National Measurement Institute, Australia on 27 Oct. 2011 under Accession Number V11/022946; wherein the strain of *Lactobacillus rapi* is *Lactobacillus rapi* Lr24 deposited with National Measurement Institute, Australia on 27 Oct. 2011 under Accession Number V11/022947; wherein the strain of *Lactobacillus zeae* is *Lactobacillus zeae* Lz26 deposited with National Measurement Institute, Australia on 27 Oct. 2011 under Accession Number V11/022948; wherein the strain of *Acetobacter fabarum* is *Acetobacter fabarum* Afl5 deposited with the National Measurement Institute, Australia on 27 Oct. 2011 under Accession Number V11/022943, and/or wherein the strain of *Candida ethanolica* is *Candida ethanolica* Ce31 deposited with the National Measurement Institute, Australia on 27 Oct. 2011 under Accession Number V11/022944.

3. The method according to claim 1, wherein one or more of the strains in the fertilizer composition are encapsulated.

4. The method according to claim wherein the plants are pasture plants, crop plants or ornamental plants.

5. The method according to claim 4, wherein the crop plants are a human or animal food crop, or crop for use as fuel or for pharmaceutical production.

6. The method according to claim 5, wherein the food crop is a fruit, vegetable, nut, seed, or grain crop.

7. The method according to claim 1, wherein the microbial fertilizer composition further comprises one or more trace elements, one or more humic substances, molasses and/or phosphoric acid.

8. The method according to claim 7, wherein the microbial fertilizer composition comprises by weight at least about 2% trace elements, at least about 0.3% humate, at least about 3% molasses and at least about 0.1% phosphoric acid.

9. A method, comprising:
   i) providing a microbial fertilizer composition comprising strains of *Lactobacillus parafarraginis, Lactobacillus buchneri, Lactobacillus rapi, Lactobacillus zeae, Acetobacter fabarum,* and *Candida ethanolica;*
   ii) treating soil with an amount of the microbial fertilizer composition; and
   iii) growing plant seeds or seedlings in the treated soil to produce plants,
   wherein the amount of the microbial fertilizer composition is effective to increase plant growth and/or productivity of the plants.

10. The method according to claim 9, wherein the strain of *Lactobacillus parafarraginis* is *Lactobacillus parafarraginis* Lp18 deposited with National Measurement Institute, Australia on 27 October 2011 under Accession Number V11/022945; wherein the strain of *Lactobacillus buchneri* is *Lactobacillus buchneri* Lb23 deposited with National Measurement Institute, Australia on 27 Oct. 2011 under Accession Number V11/022946; wherein the strain of *Lactobacillus rapi* is *Lactobacillus rapi* Lr24 deposited with National Measurement Institute, Australia on 27 Oct. 2011 under Accession Number V11/022947; wherein the strain of *Lactobacillus zeae* is *Lactobacillus zeae* Lz26 deposited with National Measurement Institute, Australia on 27 Oct. 2011 under Accession Number V11/022948; wherein the strain of *Acetobacter fabarum* is *Acetobacter fabarum* Afl5 deposited with the National Measurement Institute, Australia on 27 Oct. 2011 under Accession Number V11/022943; and/or wherein the strain of *Candida ethanolica* is *Candida ethanolica* Ce31 deposited with the National Measurement Institute, Australia on 27 October 2011 under Accession Number V11/022944.

11. The method according to claim 9, wherein one or more of the strains in the fertilizer composition are encapsulated.

12. The method according to claim 9, wherein the plant seeds or seedlings are of pasture plants, crop plants, or ornamental plants.

13. The method according to claim 12, wherein the crop plants are a human or animal food crop, or a crop for use as fuel or for pharmaceutical production.

14. The method according to claim 13, wherein the food crop is a fruit, vegetable, nut, seed, or grain crop.

15. The method according to claim 9, wherein the microbial fertilizer composition further comprises one or more trace elements, one or more humic substances, molasses, and/or phosphoric acid.

16. The method according to claim 9, wherein the microbial fertilizer composition further comprises by weight at least about 2% trace elements, at least about 0.3% humate, at least about 3% molasses and at least about 0.1% phosphoric acid.

17. A method, comprising:
   i) providing a microbial fertilizer composition comprising strains of *Lactobacillus parafarraginis, Lactobacillus buchneri, Lactobacillus rapi, Lactobacillus zeae, Acetobacter fabarum,* and *Candida ethanolica;*
   ii) treating soil or pasture with an amount of the microbial fertilizer composition, and iii) growing pasture plants in the treated soil or pasture;
wherein the amount of the microbial fertilizer composition is effective to increase plant growth, plant yield, and/or plant nutrient content of the pasture plants.

* * * * *